(12) United States Patent
Heinecke et al.

(10) Patent No.: US 6,264,976 B1
(45) Date of Patent: Jul. 24, 2001

(54) ABSORBENT PAD DRESSING FRAME DELIVERY SYSTEM

(75) Inventors: Steven B. Heinecke, New Richmond, WI (US); Wayne L. Liedtke, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/450,242

(22) Filed: Nov. 29, 1999

(51) Int. Cl.[7] .............................. A61F 13/00; A61L 15/00
(52) U.S. Cl. ..................... 424/443; 424/445; 424/446; 424/447; 424/448; 424/449
(58) Field of Search .................................... 424/449, 448, 424/443

(56) References Cited

U.S. PATENT DOCUMENTS

| | | | |
|---|---|---|---|
| Re. 24,906 | 12/1960 | Ulrich | 206/59 |
| Re. 33,353 | 9/1990 | Heinecke | 428/40 |
| D. 408,541 | 4/1999 | Dunshee et al. | D24/189 |
| D. 409,754 | 5/1999 | Dunshee et al. | D24/189 |
| D. 410,087 | 5/1999 | Dunshee et al. | D24/189 |
| 3,389,827 | 6/1968 | Abere et al. | 220/53 |
| 4,112,213 | 9/1978 | Waldman | 526/279 |
| 4,231,369 | 11/1980 | Sorensen et al. | 128/283 |
| 4,310,509 | 1/1982 | Berglund et al. | 424/28 |
| 4,323,557 | 4/1982 | Rosso et al. | 424/28 |
| 4,373,519 | 2/1983 | Errede et al. | 128/156 |
| 4,472,480 | 9/1984 | Olson | 428/332 |
| 4,477,325 | 10/1984 | Osburn | 204/159.12 |
| 4,499,896 | 2/1985 | Heinecke | 128/156 |
| 4,551,490 | 11/1985 | Doyle et al. | 524/22 |
| 4,565,663 | 1/1986 | Errede et al. | 264/120 |
| 4,598,004 | 7/1986 | Heinecke | 428/40 |
| 4,693,776 | 9/1987 | Krampe et al. | 156/327 |
| 4,737,410 | 4/1988 | Kantner | 428/343 |
| 4,738,257 | 4/1988 | Meyer et al. | 128/156 |
| 4,944,040 | 7/1990 | Riedel et al. | 2/15 |
| 4,952,618 * | 8/1990 | Olsen | 524/17 |
| 5,009,224 | 4/1991 | Cole | 128/156 |

(List continued on next page.)

FOREIGN PATENT DOCUMENTS

| | | |
|---|---|---|
| 0 051 935 A2 | 5/1982 | (EP) . |
| 0 051 935 B1 | 5/1982 | (EP) . |
| 0 368 541 B1 | 5/1990 | (EP) . |
| WO 84/03837 | 10/1984 | (WO) . |
| WO 94/21207 * | 9/1994 | (WO) ............ A61F/13/02 |
| WO 98/00080 | 1/1998 | (WO) . |
| WO 98/15245 | 4/1998 | (WO) . |
| WO 99/27975 | 6/1999 | (WO) . |

OTHER PUBLICATIONS

*Handbook of Pressure–Sensitive Adhesive Technology*, Chapter 18, "Silicone Release Coatingd", Mary D. Fey and John E. Wilson, pp. 384–403, Van Nostrand Reinhold Co., 1982.

Primary Examiner—Thurman K. Page
Assistant Examiner—Isis Ghali
(74) Attorney, Agent, or Firm—Robert W. Sprague (57) ABSTRACT

A wound dressing and delivery system comprising carrier frame that overlaps a heavy absorbent pad on a thin backing of the wound dressing (with the backing sandwiched between the pad and carrier frame) so that the carrier frame and absorbent pad support (e.g., rigidify) the backing to facilitate handling. The carrier frame also has a window over the absorbent pad. Adhesive is provided one major surface of the backing, and the absorbent pad is provided on this major surface. The carrier frame is provided on the opposite major surface to the absorbent pad. The backing is preferably a very thin transparent or translucent elastic polymeric film, and the absorbent pad is relative thick, heavy and stiff and preferably includes hydrocolloid or hydrogel materials. Slits may be provided in the carrier frame to permit one of more portions of the frame to be removed from the backing without removing the entire frame from the backing.

18 Claims, 5 Drawing Sheets

U.S. PATENT DOCUMENTS

| | | | |
|---|---|---|---|
| 5,088,483 | 2/1992 | Heinecke | 602/46 |
| 5,153,040 | 10/1992 | Faasse, Jr. | 428/40 |
| 5,160,315 | 11/1992 | Heinecke et al. | 602/57 |
| 5,520,629 | 5/1996 | Heinecke et al. | 602/57 |
| 5,531,855 | 7/1996 | Heinecke et al. | 156/252 |
| 5,622,711 * | 4/1997 | Chen | 424/445 |
| 5,633,010 | 5/1997 | Chen | 424/448 |
| 5,733,570 | 3/1998 | Chen et al. | 424/445 |
| 5,738,642 * | 4/1998 | Heinecke et al. | 602/58 |
| 5,849,325 | 12/1998 | Heinecke et al. | 424/443 |
| 5,968,533 * | 10/1999 | Porter et al. | 424/401 |

\* cited by examiner

ABSORBENT PAD DRESSING FRAME DELIVERY SYSTEM

The invention relates to wound dressings, and more particularly to a thin film composite dressing with an absorbent pad. and a frame delivery system for the dressing

BACKGROUND OF THE INVENTION

Hydrocolloid adhesive compositions that are formed as wound dressings have been known for many years. Typically, these compositions comprise a blend of a polymer matrix, such as a rubbery elastomer like polyisobutylene, in combination with one or more water-soluble or water-swellable hydrocolloids, such as a dry powdered mixture of pectin, gelatin and carboxymethylcllulose. The adhesive composition is usually coated on at least one surface of a water-insoluble film to form a relatively thick, heavy wound dressing.

Commercially available examples of hydrocolloid wound dressings include "DUODERM™" and "DUODERM™ EXTRA-THIN" wound dressing (a product of Convatec; Squibb and Sons, Inc., Princeton, N.J. believed to be a KRATON™-based composition); TEGASORB™ wound dressing (a product of Minnesota Mining and Manufacturing Company, St. Paul, Minn. a polyisobutylene-based composition); RESTORE™ wound dressing (a product of Hollister, Inc., Libertyville, Ill. believed to be an ethylene vinyl acetate (EVA)-based composition); and COMFEEL™ wound dressing (a product of Coloplast International, Espergaerde, Denmark; believed to be a KRATON™ -based composition). See, also, U.S. Pat. Nos. 4,231,369; 4,477, 325; 4,551,490; 4,738,257 and 5,633,010.

The delivery system for most of the above examples provide a simple release liner to protect the tacky hydrocolloid surface. One exception to this class is the TEGASORB™ wound dressing. This product has a thin, adhesive coated polymeric backing extended beyond the edges of the absorbent hydrocolloid pad to form a border that will adhere to the skin and provide barrier to outside contamination as well as keep wound fluid contained providing for a longer wear tune.

A successful delivery system has been used on Tegaderm$^{TM}$ transparent dressings (a product of Minnesota Mining and Manufacturing Company, St. Paul, Minn. The Tegader™ dressing comprises a thin. polyurethane with an adhesive on one surface and a carrier or frame that facilitates application. The Tegaderm™ transparent dressing, however, does not include a hydrocolloid or absorbent pad. See, also, U.S. Pat. No. 5,531,855.

PCT Patent Publication No. WO 98/00080 shows the combination of a package and a medical adhesive composite, such as a dressing. See, also, U.S. Design Pat. Nos. 408,541; 409,754 and 410,087 and U.S. Pat. No. U.S. Ser. No. 08/887,523, filed Jul. 2, 1997), which are incorporated herein by reference.

SUMMARY OF THE INVENTION

The invention provides an absorbent dressing and delivery system that facilitates handling the extremely thin, flexible film border of the dressing during delivery to prevent wrinkling and adhering the film of the dressing to itself, which otherwise would interfere with the smooth, aseptic application of the dressing to a patient's skin.

The island dressing composite of the invention provides a carrier delivered dressing having a conformable backing with a pressure sensitive adhesive coated on a bottom and a absorbent pad positioned on the adhesive, and which is supported by a removable carrier attached to the top face of the backing. In particular, the present invention overcomes the problems discussed above by securing the carrier to the top face of the backing with an overlapping form.

Furthermore, in one embodiment, the method and apparatus of the present invention provide such a carrier delivered dressing in which the window is optionally removed prior to use by the consumer, thereby minimizing the steps necessary to apply the dressings and reducing the waste stream at the consumer level.

In particular, the present invention provides an adhesive composite dressing comprising (a) a conformable backing having top and bottom faces; (b) a pressure sensitive adhesive coated on at least a portion of the bottom face of the backing; (c) a absorbent or medicated pad primarily in the center portion; (d) a liner releasably adhered to the pressure sensitive adhesive opposite the backing; and (e) a carrier releasably attached to and covering at least a portion of the top face of the backing, the carrier being nonpermanently attached to the backing and a cut in the carrier substantially defining a window proximate a center of the carrier and overlapping at least a portion of the pad, the carrier further being formed of material substantially more rigid than the backing to provide rigidity to the adhesive composite. The composite dressing may also include an optional low adhesion coating on the top face of the backing, in between the carrier and the top face of the backing.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
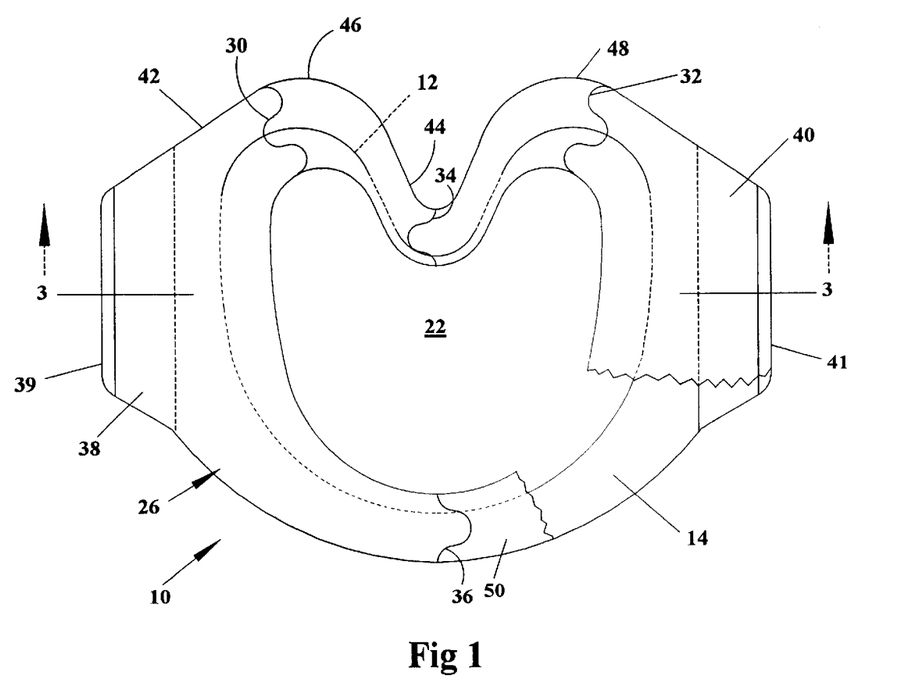
FIG. 1 is a top plan view of a preferred embodiment of the absorbent pad dressing and delivery system according to the invention.
Figure 2:
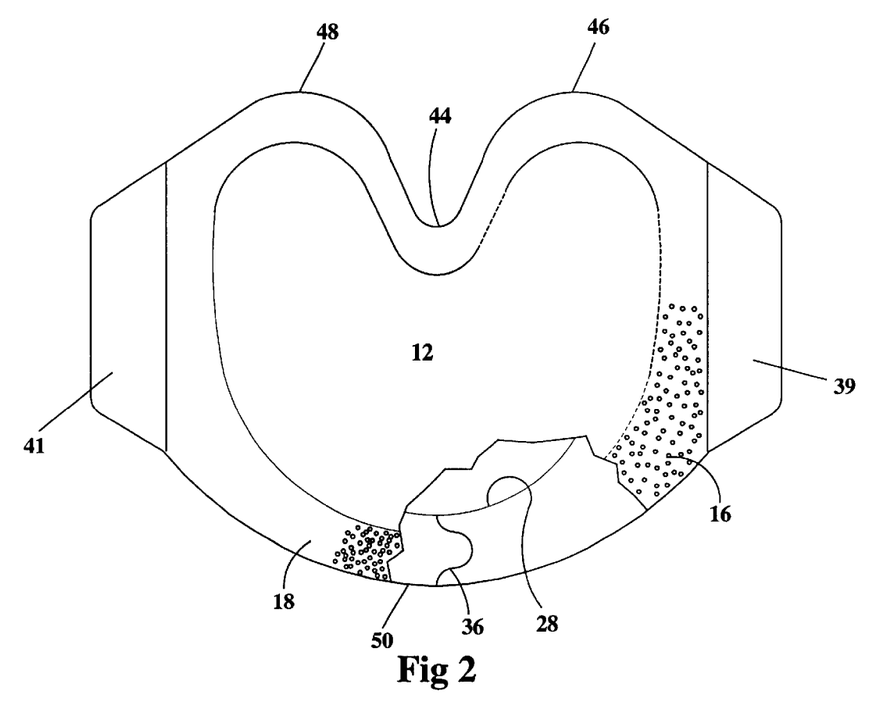
FIG. 2 is a bottom plan view of the dressing and delivery system of FIG. 1.
Figure 3:
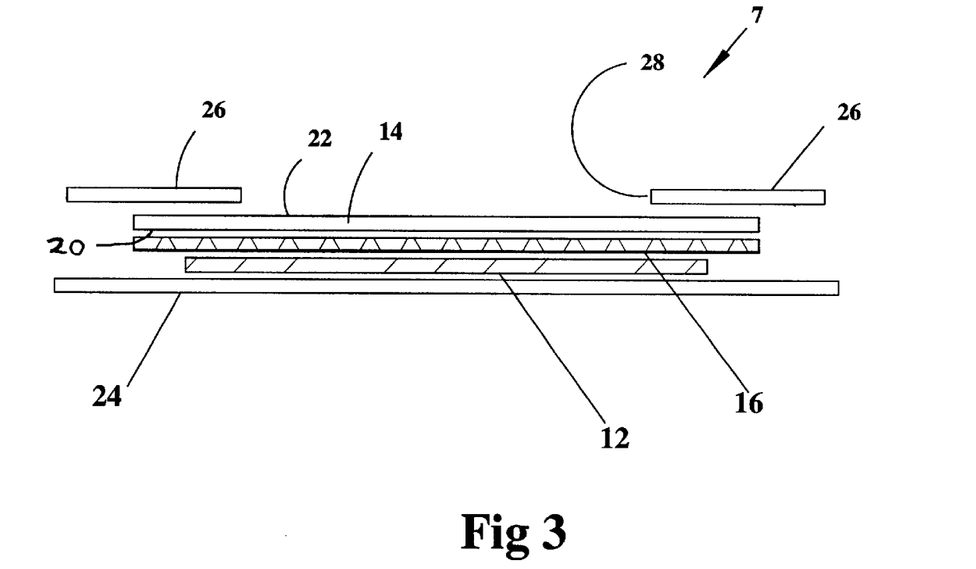
FIG. 3 is a side schematic view of the dressing of FIGS. 1 and 2 taken substantially along line 3—3 of FIG. 1.

FIGS. 1–3 depict a preferred embodiment of the absorbent pad dressing and delivery system designated in its entirety by the reference numeral 10. The delivery system of this invention is particularly useful in connection with a dressing in which a relatively heavy or stiff absorbent pad 12 is positioned on a conformable backing 14 that is light and flexible relative to the pad 12. In this preferred embodiment, both of the absorbent pad 12 and the backing 14 have a generally kidney-shape or outline, and are particularly designed for use a sacral dressing, although the invention is not limited to this shape or to sacral dressings. The preferred backing 14 is a transparent or translucent elastic film.

Preferably, a pressure sensitive adhesive (PSA) 16 is provided on along one major surface 18 of the backing 14, and a low adhesion coating (low adhesion backsize or LAB) 20 is provided on the other major surface 22 of the backing 14. A description of a preferred low adhesion coating for use with the present invention can be found in U.S. Pat. No. 5,531,855 (Example 1), which is compatible with a heat seal bond described below, The low adhesion coating 20 reduces dressing changes due to unwanted dressing removal when other tapes or devices arc placed on the dressing 10 and removed, and reduces the surface friction of the dressing 10 on linen or other fabrics, thereby offering additional protection against the accidental removal of dressing 10

Major surface 18 is sometimes referred to as the "bottom face" or "first major surface" of the backing, 14, and major surface 22 is sometimes referred to as the "top face" or "second major surface" of the backing 14.

A release liner 24 is attached to the exposed surface of pressure-sensitive adhesive 16 on the bottom face 18 of the backing 14. The release liner 24 covers the PSA until the consumer is ready to apply the dressing 10. The release liner 24 may be a single piece or multiple piece release liner, and may be part of or laminated to the package (not shown) containing the dressing, or merely enclosed along with the dressing 10 within the package.

The absorbent pad 12 of this dressing 10 is sometimes referred to as an "island pad" because the backing 14 extends substantially beyond the absorbent pad 12, typically beyond the entire periphery of the pad 12. For example, the length and width of the backing could be 16.1 cm×21.9 cm, and the length and width of the absorbent pad could be 12.3 cm×13.9 cm. The pressure sensitive adhesive 16 on the peripheral portion of the backing 14 not covered by the island pad 12 may be adhered to the skin of a patient This portion of the backing 14 is thus not supported or reinforced by the relatively heavy and stiff absorbent pad 12, and absent the benefits of the invention would be difficult to handle without folding, wrinkling or otherwise adhering to itself rather than adhering to the skin.

FIG. 2 is a bottom view of dressing 10 with the liner 24 removed to expose the adhesive layer 16 and absorbent pad 12, which is disposed proximate the center of the dressing 10. Although absorbent pad 12 is shown as centered on dressing 10 and as having a kidney-shape similar to, but smaller than, the backing 14, it can take any appropriate shape aid/or can be located off center on the dressing 10 as desired.

A carrier frame 26 is attached to the top face 22 of the backing 14 over the low adhesion coating 20. Tie carrier frame 26 extends along substantially the entire periphery of the backing 14 and forms a window 28 exposing a portion of the backing 14 overlying the absorbent pad 12 with the backing 14 sandwiched between the frame 26 and absorbent pad 12.

As used herein, a first piece can be said to "overlaps" or "overlie" a second piece if it covers a portion of either the second piece, or a portion of some third piece that is covered along its opposite side by the second piece. In other words, one piece can "overlap" or "overlie" another piece even though separated by a third piece. More specifically, the carrier frame 26 can "overlap" or "overlie" the absorbent pad 12 with the backing 14 positioned between the overlapped portions of the absorbent pad 12 and carrier 24.

As used herein, the term "sandwiched" means that one layer is intermediate or between two other layers. For example, the backing 14 may be considered an intermediate layer between the carrier frame 26 and the absorbent pad 12, and thus is "sandwiched" between the frame 26 and absorbent pad 12.

The preferred arrangement is such that:

(a) One or the other major surface of the backing 14 is covered by either the absorbent pad 12 or the carrier frame 26 (or both) substantially throughout the extent of the backing 14;

(b). Substantially the entire periphery of the absorbent pad 12 is overlapped by the carrier frame 26 so that the portion of the backing 14 covered on one major surface by the absorbent pad is covered on the other major surface by the carrier frame 26, thus forming what might be considered a three-layer or double-supported "ring" (the shape of the ring is defined by the periphery of the pad 12 and the window 28 of the carrier frame 26, and in the first preferred embodiment will be generally kidney shaped); and (c) Each of the carrier frame 26 and absorbent pad 12 are substantially more rigid than the backing 14.

The carrier fame 26 is preferably attached to the second major surface 22 of the backing 14 (over low adhesion coating 20) with a heat seal bond. The beat seal bond between the carrier frame 26 and the backing 14 is stronger than the bond between the pressure sensitive adhesive 16 and the release liner 24 so that the backing 14 remains attached to the carrier frame 26 when release liner 26 is removed from the dressing 10. Once the release liner 24 and dressing, 10 are separated, only the carrier frame 26 and absorbent pad 12 support (i.e. provide rigidity to) the backing 14.

Most preferably, the carrier frame 26 has several nonlinear cuts or slits 30, 32, 34 and 36, which may be controlled depth die cut so as not to cut the backing 14. Any of the slits 30, 32, 34 br 36 provides a beginning point at which the carrier frame 26 may be lifted from backing 14 and peeled away Several nonlinear slits 30, 32, 34 and 36 strategically positioned around the frame 26 allow for distinct sections of the carrier frame 26 to be removed without removing the other sections to aid in the delivery over body contours. It is also contemplated that a section of the frame could be removed to better conform to a catheter while the non-removed sections of the frame facilitate application of a dressing over the catheter.

Although each slit 30, 32, 34 and 36 may be a linear, they are preferably nonlinear. Nonlinear slits 30, 32, 34 and 36, are believed to provide more support for the backing 14 and carrier 24 because nonlinear slits are less likely to allow the carrier 24 to fold at the slit or cut line as compared to linear cuts. If frame 26 folds along one or more of the slits 30, 32, 34 or 36, the adhesive on the backing 214 will adhere to itself rendering the dressing 210 useless. Most preferably, the slits 30, 32, 34 and 36 are provided by generally sinusoidal cuts 30, 32, 34 and 36 as shown in FIGS. 1 and 2, although other nonlinear'slits that tend to resist folding may also provide good service, such as zigzag, undulating, single or multiple tooth patterns or irregular or non symmetrical nonlinear slits.

Preferably, the frame 26 includes one or more tabs 38 and 40 extending beyond the perimeter of backing 14 to provide a means of removing the backing/frame/adhesive composite from the release liner 24 and applying the composite without contacting the adhesive 16. For example,.two tabs 38 and 40 extend longitudinally outwardly from opposite ends of the frame 26 to provide a structure that can be gripped by fingers to peel the dressing from the release liner 24. Most preferably, the release liner 24 includes two tabs 39 and 41 corresponding to the tabs 38 and 40 of the frame 264 so that one tab (e.g., 39) of the liner 24 and one tab (e.g., 38) of the fire 26 may be grasped to separate the dressing and frame from the release liner 24.

FIGS. 1–3 depict a preferred kidney-shaped dressing 10, which is particularly designed to be a sacral dressing. The periphery 42 of preferred embodiment of the dressing 10 has a concave edge portion 44, two minor convex edge portions 46 and 48 surrounding the concave edge portion 44 and a major convex edge portion 50 defining the edge of the dressing opposite the concave edge portion 44. The minor convex edge portions 46 and 48 and concave edge portion 44 thus form one side edge of the frame 26 extending between the tabs 38 and 40, and the major edge portion 50 forms the opposite side edge of the frame extending between the tabs 38 and 40.

The opposite ends of the concave edge portion 44 may be considered as being defined approximately at the apex or pinnacle of each of the minor convex edge portions 46 and 48. Such pinnacles are the point of inflection where the edge of the dressing starts to curve inwardly to form the concave edge portion 44. The nadir of the concave edge portion 44 is the point of inflection of the concave edge portion 44. The nadir of the concave edge portion 44 and the apex of the major convex edge portion 50 define a line of symmetry that bisects the frame 26 (and dressing 10) into two substantially mirror image parts.

Most preferably, two of the slits 30 and 32 are arranged generally adjacent the opposite ends of the concave edge portion 38 to facilitate removal of the portions.46 and 48 of the frame adjacent the concave edge portion 38, one slit 34 extending inwardly of the frame 26 from generally adjacent the nadir of the concave edge portion 38, and one slit 36 extending inwardly of the frame 26 from generally adjacent the apex of the major convex edge portion. The arrangement is such that the slit 34 adjacent the nadir of the concave edge portion 38 and the slit 36 adjacent the apex of the major convex edge portion 50 extend substantially in directions along a common line (in the sense that nonlinear slits can be considered to define a direction).

Slits 34 and 36 in FIG. 1 are depicted as each having the curve formed by a tab on one piece of the frame 26 and a concave edge on the adjacent piece receiving the tab. Most preferably, in this example, the tabs forming slits 34 and 36 extend toward opposite ends of the frame 26.

The window 28 may be cut (e.g., controlled depth die cut) from a carrier blank to form a carrier frame 24 having a window exposing a portion of the top surface of the backing 14. The out or window portion of the carder blank may be either removed during manufacturing or by the consumer. Removal during manufacturing eliminates one step in the delivery process for previously known window style dressings and reduces the waste stream at the consumer level. Some customers, however, prefer that the portion of the carrier overing window 28 remains intact until the dressing 10 reaches the consumer.

Preferably, the absorbent pad 12 comprises hydrocolloid and hydrogel pad 12 having a thickness of at least 1 mm (e.g., most preferably 3–9 mm), and the backing 14 comprises a transparent elastic polymeric film (e.g., urethane) having a thickness no greater than 0.1 mm (e.g., most preferably 0.021–0.051 mm). It will be appreciated that in this preferred embodiment the pad 12 is much thicker, stiffer and heavier than the film backing 14.

Figure 4:
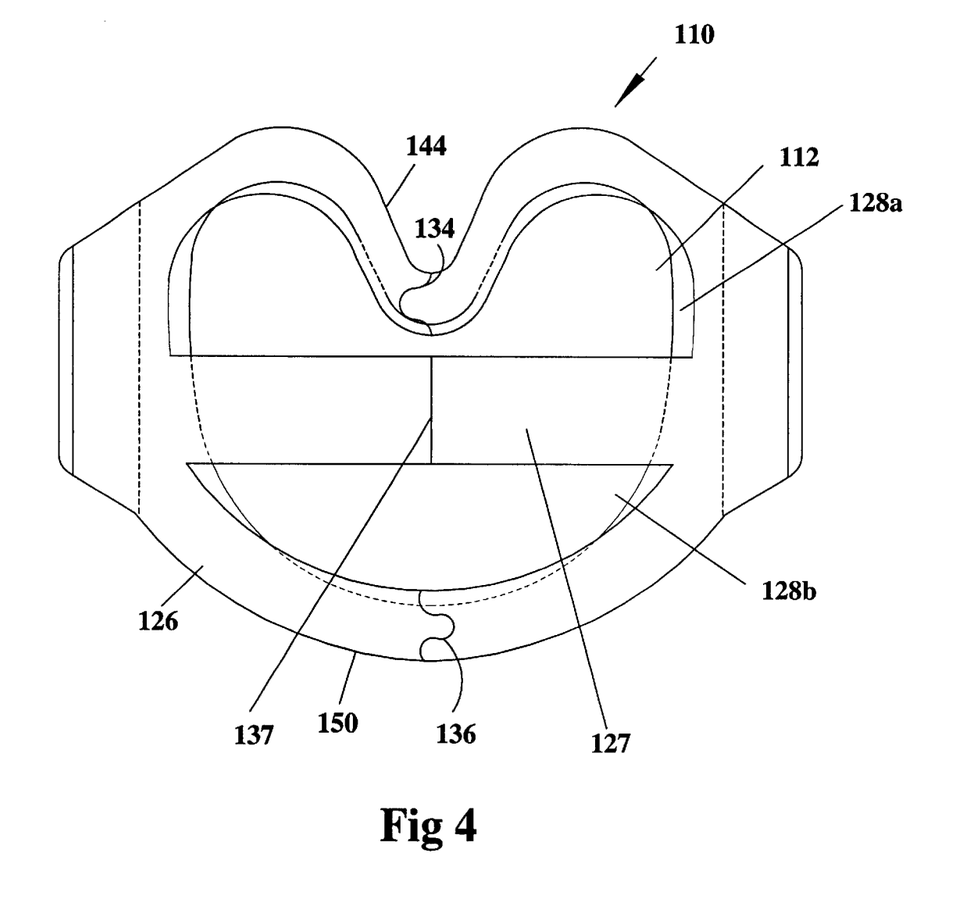
FIG. 4 is a top plan view of an alternate preferred embodiment of the absorbent pad dressing and delivery system according to the invention.

Features of the embodiment in FIG. 4 that are similar to the features of FIGS. 1–3 are designated by, the same last two digits of the reference numbers but with the addition of "100".

FIG. 4 depicts an alternative preferred embodiment of the invention similar in some respects to the embodiment of. FIGS. 1–3 except that (a) the carrier frame 126 overlaps only a portion of the:absorbent pad 112, and (b) a bridge 127 is provided on the frame 126 extending along the length of the dressing to provide additional support of the frame 126 by the absorbent pad 112. A slit 13.7 may be provided across the bridge 127 to facilitate removing one side of the bridge and the adjacent frame portion before the other side of the bridge and its adjacent frame portion. The slit 137 may be linear or non-linear but is depicted as linear because it is believed that absorbent pad 112 provides sufficient support for this slit 137 to be linear. The slit 137 is shown as extending generally along a common line with the apex and nadir of the major convex edge portion 150 and concave edge portion 144, but could be offset in either direction from this common line In this embodiment the window 128a and 128b comprises two window portions 128a and 129b separated by the bridge 127.

Figure 5:
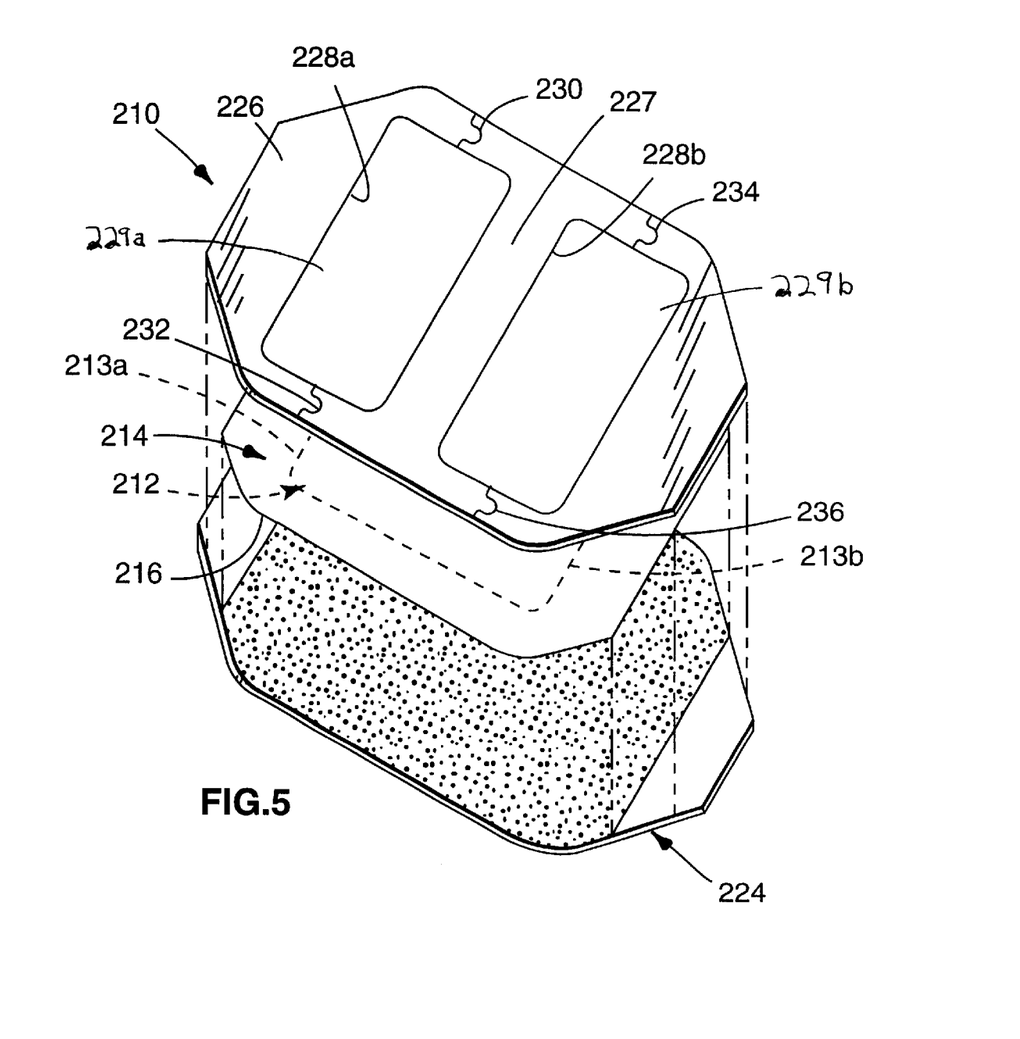
FIG. 5 is a perspective, exploded view of another alternate preferred embodiment of the absorbent pad dressing and delivery system according to the invention.

Features of the embodiment of FIG. 5 that are similar to the features of FIGS. 1–3 are designated by the same last two digits of the reference numbers but with the addition of "200".

FIG. 5 depicts a second alternative preferred embodiment of the invention similar in some respects to the embodiments of FIGS. 1–4 except that (a) The absorbent pad 212 is only overlapped by the frame 226 along the opposite ends 213a and 213b of the absorbent pad, and across an intermediate portion of the absorbent pad 212 by a bridge 227, thus providing portions of the. windows 228a and 228b that do not overly the absorbent pad 212;

(b) The backing 214 has a generally rectangular shape with the corners cut off;

(c) The windows 228a and 228b are each generally rectangular shaped with longitudinal axes that a substantially parallel with one another and substantially perpendicular to tee longitudinal axis of the frame 226;

(d) The absorbent pad 212 has a generally rectangular shape having a longitudinal axis substantially parallel with the longitudinal axis of the backing 214 but substantially perpendicular to the longitudinal axes of the windows 228a and 229b;

(e) Four slits 230, 232, 234 and 236 are provided along the long side edges of the carrier frame 226 and are arranged in two sets of two slits (230 and 232, 234 and 236) with each set of slits extending generally in the longitudinal direction of the windows (perpendicular to the longitudinal direction of the frame 226);

(f) The bridge 227 does not include an intermediate slit; and (g) The carrier pieces 229a and 229b covering the windows 228a and 228b are depicted as staying in place until removed by the consumer.

An alternative embodiment of the invention is also contemplated in which the carrier frame has an opening such that the frame extends slightly less t completely around the perimeter of the backing. The opening would allow the dressing to be placed over catheters or other devices while still attached to the frame to increase the ease of handling of backing.

The described embodiments are illustrative examples, and the features of one embodiment may be used in connection with the other embodiments. For example, a bridge could be added to the embodiment of FIGS. 1–3.

Preferred Backing Materials

Suitable backings 14, 114 or 214 include, for example, nonwoven fibrous webs, woven fibrous webs, knits, films and other familiar backing materials. The. preferred backing materials are translucent or transparent polymeric elastic films. Most preferably, the backing is a high moisture vapor permeable film backings. U.S. Pat. No. 3,645,835, the disclosures of which are hereby incorporated by reference, describe methods of making such films and methods for testing their permeability.

Preferably, the film/adhesive composite should transmit moisture vapor at a rate equal to or greater than human skin. Preferably, the adhesive coated film transmits moisture vapor at a rate of at least 300 $g/m^2/24$ hrs/37° C./100–10% RH, more preferably at least 700 $g/m^2/24$ hrs/37° C./100–10% RH, and most preferably at least 2000 $g/m^2/24$ hrs/37° C./100–10% RH using the inverted cup method.

The backing is preferably conformable to anatomical surfaces. As such, when the backing is applied to an anatomical surface, it conforms to the surface even when the surface is moved. The preferred backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

A description of this characteristic of backings preferred. for use with the present invention can be found in issued U.S. Pat. Nos. 5,088,483 and 5,160,315, the disclosures of which are hereby incorporated by reference. Particularly preferred backings are elastomeric polyurethane, co-polyester, or polyether block amide films. These films combine the desirable properties of resiliency, high moisture vapor permeability, and transparency found in preferred backings.

Preferred Pressure Sensitive Adhesive

While any pressure sensitive adhesive 16, 116 or 216 can be used, the preferred pressure sensitive adhesive is reasonably skin compatible and "hypoallergenic", such as the acrylate copolymers described in U.S. Pat. No. RE 24,906, the disclosure of which is hereby incorporated by reference. Particularly preferred is a 97:3 iso-octyl acrylate:acrylamide copolymer. Also preferred is an 70:15:15 isooctyl acrylate: ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827, 4,112, 213, 4,310,509, and 4,323,557, the disclosures of which are hereby incorporated by reference. Inclusion of medicaments or antimicrobial agents in the adhesive is also contemplated, as described in U.S. Pat. Nos. 4,310,509 and 4,323,557 both of which are hereby incorporated by reference.

The preferred pressure sensitive adhesives described above preferably transmit moisture vapor at rate greater to or equal to that of human skin While such a characteristic can be achieved through the selection of an appropriate adhesive or through use of a nonwoven (e.g., melt blown) adhesive (as described in U.S. patent application Ser. No. 08/980,541, filed Dec. 1, 1997, U.S. patent application Ser. No. 09/201, 954, filed Dec. 2, 1998, and PCT Publication No. WO 99/27975 (all of which are incorporated herein by reference)), it is also contemplated in the present invention that other methods of achieving a high relative rate of moisture vapor transmission may be used, such as pattern coating the adhesive on the backing.

The preferred film and adhesive combinations is disclosed in U.S. Pat. No. 5,849,325 (Example 1), the disclosure of which is hereby incorporated by reference.

Preferred Absorbent Pad Materials

Absorbent pad 12, 112 or 212 can be manufactured of any of a variety of materials including, but not limited to, woven or nonwoven cotton or rayon. Absorbent pad 12 is useful for containing a number of substances, including antimicrobial agents, drugs for transdermal drug delivery, chemical indicators to monitor hormones or other substances in a patient, etc.

The preferred island pad providing an absorbent matrix includes the normal adhesives which are applied to the skin, or the hydrocolloid compositions described in U.S. Pat. Nos. 5,622,711 and 5,633,010, the disclosure of which is hereby incorporated by reference. The hydrocolloid absorbent may comprise, for example, a natural hydrocolloid, such as pectin, gelatin, or carboxymethylcellulose (CMC) (Aqualon Corp., Wilmington, Del.). a semi-synthetic hydrocolloid, such as cross-linked carboxymethylcllulose (x-link CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. Preferably, the hydrocolloid absorbent component comprises from about 5 percent to about 60 percent by weight of the adhesive composition., When preparing anti adhesive composition for use in a wound dressing the hydrocolloid absorbent preferably comprises from about 20 percent to about 40 percent by weight of the composition.

Preferred Release Liner Materials

Preferred release Liners 24, 124 or 224 can be made of kraft papers, polyethylene, polypropylene, polyester or composites of any of these materials. The liners are preferably coated with release agents such as fluorochemicals or silicones. For example, U.S. Pat. No. 4,472,480, the disclosure of which is hereby incorporated by reference, describes low surface energy perfluorochemical liners. The preferred liners are papers, polyolefin films, or polyester films coated with silicone release materials. Examples of commercially available silicone coated release papers are POLYSLIK™ silicone release papers available from Rexam Release (Bedford Park, Ill.) and silicone release papers supplied by DCP-Lohya Co. (Dixon, Ill.). The most preferred liner is 1-60BKG-157 paper liner available from DCP-Lohya, which is a super calendared Kraft paper with a water-based silicone release surface.

Other combinations of adhesives and liners are contemplated for use with embodiments according to the present invention Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the Handbook of Pressure Sensitive Adhesive Technology, Van Nostrand-Reinhold, 1982, pp. 384–403. U.S. Pat. No. 4,472,480 also describes considerations pertinent to the selection of a perfluoropolyether release liner Liners are available from a variety of manufacturers in a wide variety of proprietary formulations. Those skilled in the art will normally test those liners in simulated use conditions against an adhesive of choice to arrive at a product with the desired release characteristics.

Preferred Carrier Materials

The preferred carrier material used to supply the carrier/carrier frame 28, 128 or 228 is preferably substantially more rigid than the backing 14, 114, 214 to prevent the backing 14, 114, 214 from wrinkling during application. The carrier material can be heat-sealable to the backing 14, 114, 214, with or without the low adhesion coating described above. In general, the preferred carrier materials include, but are not limited to, polyethylene/vinyl acetate copolymer-coated papers and polyester films. One example of a preferred carrier material is a polyethylene/vinyl acetate copolymer coated super calendared Kraft paper (1-80BKG-157 PE; DCP-Lohya).

Use

In use, the liner 2.4, 124 or 224 is first removed from the dressing 10, 110 or 210 leaving the frame Z6, 126, 226/backing 14, 114, 214/pressure-sensitive adhesive 16, 116, 216/absorbent pad 12, 112, 212 composite intact. The user can then manipulate the dressing 10, 110, 210 using tabs 38, 40 on the frame 26 while viewing the area to which the dressing 10, 110, 210 will be attached through window 28, 128a /128b or 228a /228b , as the preferred backing 14, 114, 1214 is transparent or translucent.

To apply the wound dressing 10 to the sacral groove of a patient, (a) the portion(s) of the frame 26 adjacent the concave edge portion 44 of the dressing 10 (i.e. the portion (s) between slits 30 and 32) is removed from the backing 14 while leaving other portions of the frame 26 in place on the backing 14; (b) the dressing 10 is then bent to form a concave curve along the first major surface of the backing 14 with the adhesive-coated major surface 20 (bottom face) of the backing 14 adjacent the concave edge portion 44 being along the top of the concave curve; and (c) the concave edge portion 44 of the dressing 10 is inserted into the sacral groove first and the dressing 10 is adhered to the patient over a sacral wound. The rest of the frame 26 is then removed.

EXAMPLE 1

Pressure Sensitive Adhesive/Film Backing

The adhesive composition of this example features a pressure sensitive adhesive matrix blended with polymeric microspheres, and was prepared as follows (from example 1 of U.S. Pat. No. 5,849,325.

To prepare the microspheres, a monomer mixture was prepared by dissolving 4.8 g of acrylic acid, 2.4 g of Carbowaxac™ 750 acrylate (polyethylene oxide acrylate) and 113 g Lucidolf™-70 (70% benzoyl peroxide) in 232.8 g of iso-octyl acrylate. A surfactant solution was prepared by dissolving 0.75 g of sodium dodecyl benzene sulfonate in 360 g of water. The monomer mixture was then added to the surfactant solution, and the resulting mixture emulsified using a Gifford-Wood™ mixer until the droplet size was less than 5 micrometers. The emulsion was charged to a 1 liter baffled reactor, heated to 65° C., degassed with $N_2$, and allowed to react for 8 hours. Microspheres having an average diameter of about 2 micrometers were formed during the reaction period.

The adhesive matrix was prepared according to the procedures described generally in PCT Patent Publication No. WO 84/03837 using a monomer mixture containing 70 parts by weight isooctyl acrylate, 15 parts by weight acrylic acid, and 15 parts by weight Carbowax™ 750 acrylate (polyethylene oxide acrylate). The matrix was then blended with the microspheres (30 microspheres per hundred parts matrix) using a Lightening-brand mixer and applied to a release liner made of silicone-coated kraft paper.

Next, a 25 micrometer thick film of Estane™ 58237 thermoplastic polyurethane (B.F. Goodrich Co.) was extruded and laminated to the adhesive composition. The thickness of the adhesive composition was 25 microns (1 mil). A dressing was prepared according to the procedure described in Example 1 of Heinecke et al, U.S. Pat. No. 5,531,855, hereby incorporated by reference.

As various changes could be made in the above constructions, compositons and methods without departing from the scope of the invention as defined in the claims, it is intended that all matter contained in the above description or shown in the accompanying drawings be interpreted as illustrative and not in a limiting sense.

What is claimed is:

1. A wound dressing and delivery system comprising:
   a dressing comprising:
      a wound dressing comprising:
         an elastic film backing having first and second major surfaces and a substantially kidney-shaped periphery;
         an adhesive on the first major surface of the backing; and
         a substantially kidney-shaped absorbent pad on the first major surface of the backing, the absorbent pad being having a size and position along the backing such that the periphery of the backing extends substantially beyond the absorbent pad; and
      a delivery system comprising:
         a frame removably mounted on the second major surface adjacent the periphery of the backing, the frame overlapping the absorbent pad with the backing sandwiched between the frame and absorbent pad, the frame defining a window overlapping a portion of the absorbent pad, the frame being substantially more rigid than the backing to facilitate handling the dressing, the frame including a plurality of slits that permit one of more portions of the frame to be removed from the backing without removing the entire frame from the backing.

2. The wound dressing and delivery system according to claim 1 further comprising a release liner substantially covering the absorbent pad and the first major surface of the backing, the adhesive on the first surface of the backing tending to adhere to the release liner less than the frame tends to adhere to the second major surface of the backing.

3. The wound dressing and delivery system according to claim 2 where in the dressing is a sacral dressing having a periphery with a concave edge portion, the concave edge portion having opposite ends, the two slits being arranged adjacent opposite ends of the concave edge portion to facilitate removal of the portion of the frame adjacent the concave edge portion of the dressing.

4. The wound dressing and delivery system according to claim 1 wherein the absorbent pad comprises a hydrocolloid and hydrogel pad having a thickness of at least 1 mm, and the backing comprises an elastic film having a thickness no greater than 0.1 mm.

5. The wound dressing and delivery system according to claim 4 wherein the hydrocolloid and hydrogel pad has a thickness of approximately 3–9 mm, and the elastic film has a thickness of approximately 0.021–0.05 mm.

6. A method of applying the wound dressing of claim 3 to the sacral groove of a patient, the method comprising the following steps:

(a) removing the portion of the frame adjacent the concave edge portion of the dressing from the backing while leaving other portions of the frame in place on the backing;

(b) bending the dressing to form a concave curve along the first major surface of the backing with the concave edge portion along the top of the concave curve; and (c) inserting the concave edge portion of the dressing into the sacral groove first and adhering the dressing to the patient over a sacral wound.

7. The wound dressing and delivery system according to claim 1 wherein the absorbent pad comprises a hydrocolloid absorbent sheet material.

8. The wound dressing and delivery system according to claim 1 wherein the absorbent pad comprises a foam pad.

9. The wound dressing and delivery system according to claim 1 wherein the slits are non-linear.

10. The wound dressing and delivery system according to claim 9 wherein the slits have a substantially sinusoidal curve.

11. The wound dressing and delivery system according to claim 1 wherein the elastic film backing comprises a transparent or translucent polymeric film.

12. The wound dressing and delivery system according to claim 1 wherein the adhesive on the first major surface of the backing comprises a pressure sensitive adhesive.

13. The wound dressing and delivery system according to claim 1 wherein the frame is attached to the second major surface of the backing with a heat seal bond.

14. The wound dressing and delivery system according to claim 1 wherein the elastic film backing comprises a high moisture vapor permeable film.

15. The wound dressing and delivery system according to claim 1 wherein the elastic film backing and the adhesive on the first major surface of the backing together transmit moisture vapor at a rate of at least 300 $g/m^2/24$ hrs/37° C./100–10% RH.

16. The wound dressing and delivery system according to claim 1 wherein the elastic film backing and the adhesive on the first major surface of the backing together transmit moisture vapor at a rate of at least 700$g/m^2/24$ hrs/37° C./100–10% RH.

17. The wound dressing and delivery system according to claim 1 wherein the elastic film backing and the adhesive on the first major surface of the backing together transmit moisture vapor at a rate of at least 2000 $g/m^2/24$ hrs/37° C./100–10% RH.

18. The wound dressing and delivery system according to claim 1 wherein the elastic film backing comprises elastomeric polyurethane, co-polyester, or polyether block amide films.

\* \* \* \* \*

UNITED STATES PATENT AND TRADEMARK OFFICE
CERTIFICATE OF CORRECTION

PATENT NO. : 6,264,976 B1
DATED : July 24, 2001
INVENTOR(S) : Heinecke, Steven B.

It is certified that error appears in the above-identified patent and that said Letters Patent is hereby corrected as shown below:

Title page,
Item [56], References Cited, OTHER PUBLICATIONS, delete "Coatingd" and insert in place thereof -- Coatings --.

Column 1,
Line 6, delete ".".
Line 6, after "pad" insert -- . --.
Line 16, delete "carboxymethylcllulose" and insert in place thereof
-- carboxymethylcellulose --.
Line 19, after "N.J." insert -- ; --.
Line 28, after "Ill." insert -- ; --.
Line 42, delete "tune" and insert in place thereof -- time --.
Line 46, delete "Tegader$^{TM}$" and insert in place thereof -- Tegaderm$^{TM}$ --.
Line 46, delete ".".

Column 3,
Line 14, delete "," and insert in place thereof -- . --.
Line 16, delete "arc" and insert in place thereof -- are --.
Line 19, after "10" insert -- . --.
Line 21, delete ",".
Line 53, delete "off center" and insert in place thereof -- off-center --.
Line 56, delete "Tie" and insert in place thereof -- The --.
Line 62, delete "overlaps" and insert in place thereof -- overlap --.

Column 4,
Line 16, delete ".".
Line 28, delete "fame" and insert in place thereof -- frame --.
Line 30, delete "beat" and insert in place thereof -- heat --.
Line 42, delete "br" and insert in place thereof -- and --.
Line 44, after "away" insert -- . --.
Line 62, delete "nonlinear'" and insert -- nonlinear --.

Column 5,
Line 3, delete "For example,." and insert in place thereof -- For example, --.
Line 8, delete "264" and insert in place thereof -- 26 --.
Line 10, delete "fire" and insert in place thereof -- frame --.
Line 37, delete "portions." and insert in place thereof -- portions --.
Line 56, delete "out" and insert in place thereof -- cut --.
Line 56, delete "carder" and insert in place thereof -- carrier --.
Line 62, delete "overing" and insert in place thereof -- covering --.

UNITED STATES PATENT AND TRADEMARK OFFICE
CERTIFICATE OF CORRECTION

PATENT NO.    : 6,264,976 B1
DATED         : July 24, 2001
INVENTOR(S)   : Heinecke, Steven B.

It is certified that error appears in the above-identified patent and that said Letters Patent is hereby corrected as shown below:

Column 6,
Line 6, delete "by," and insert in place thereof -- by --.

Column 7,
Line 11, delete "The." and insert in place thereof -- The --.
Line 34, delete "preferred." and insert in place thereof -- preferred --.
Line 62, delete "skin" and insert in place thereof -- skin. --.

Column 8,
Line 25, delete "(x-link CMC)" and insert in place thereof -- (X-link CMC) --.
Line 31, delete "composition.," and insert in place thereof -- composition. --.
Line 32, delete "anti" and insert in place thereof -- an --.
Line 55, delete "invention" and insert in place thereof -- invention. --.
Line 64, delete "liner" and insert in place thereof -- liner. --.

Column 9,
Line 16, delete "2.4" and insert in place thereof -- 24 --.
Line 17, delete "Z6" and insert in place thereof -- 26 --.
Line 47, delete "Carbowaxac$^{TM}$" and insert in place thereof -- Carbowax$^{TM}$ --.
Line 48, delete "113 g Lucidolf$^{TM}$" and insert in place thereof -- 1.13 g Lucidol$^{TM}$ --.

Column 10,
Line 60, delete "-0.05 mm." and insert in place thereof -- 0.051 mm. --.

Signed and Sealed this

Eighth Day of October, 2002

*Attest:*

*Attesting Officer*

JAMES E. ROGAN
*Director of the United States Patent and Trademark Office*